United States Patent [19]
Maas

[11] 3,968,430
[45] July 6, 1976

[54] INSTALLATION FOR THE DETECTION AND PROCESSING OF ELECTRICAL SIGNALS

[75] Inventor: Michael Maas, Erlangen, Germany

[73] Assignee: Siemens Aktiengesellschaft, Erlangen, Germany

[22] Filed: Dec. 6, 1974

[21] Appl. No.: 530,354

[30] Foreign Application Priority Data
Dec. 13, 1973  Germany............................ 2362063

[52] U.S. Cl. .......................... 324/77 B; 128/2.06 A; 128/2.05 P; 324/77 E
[51] Int. Cl.² ......................................... G01R 23/16
[58] Field of Search .............. 324/77 B, 77 D, 77 E, 324/77 F, 78 E, 78 F, 78 Z; 128/2.05 P, 2.05 R, 2.05 T, 2.06 A, 2.06 B, 2.06 E, 2.06 F, 2.06 R

[56] References Cited
UNITED STATES PATENTS

| | | | |
|---|---|---|---|
| 3,293,609 | 12/1966 | Martin................. | 324/77 E |
| 3,614,673 | 10/1971 | SuaKang ............. | 324/77 E |
| 3,823,708 | 7/1974 | Lawhorn................ | 128/2.06 A |
| 3,831,088 | 8/1974 | Ort...................... | 324/77 E |
| 3,835,837 | 9/1974 | Peek.................... | 128/2.05 P |

Primary Examiner—R. V. Rolinec
Assistant Examiner—Michael J. Tokar
Attorney, Agent, or Firm—Haseltine, Lake & Waters

[57] ABSTRACT

An installation for the detection and, respectively, processing of electrical signals, in particular, physiological measuring signals, for example EKG, through the intermediary of a filter arrangement located in the measuring signal channel which is determinative of desired frequency components of the signals. The filter arrangement encompasses controllable means for the variation of the frequency range, as well as for the damping of the transmitted signal components; and which provides a control installation for effecting the control of the controllable means in dependence of the signal amplitudes in the sense whereby the transmission frequencies of the filter arrangement at signals with, in the normal case, relatively high or in contrast therewith still higher signal amplitude components, at an increase of the transmission damping, may be displaced in the direction of frequencies which are essentially significant for these high signal amplitude components; and for signals with abnormally low signal amplitude components, at a reduction of the transmission damping, may be displaced in the direction of frequencies which are essentially significant for these low signal amplitude components.

21 Claims, 1 Drawing Figure

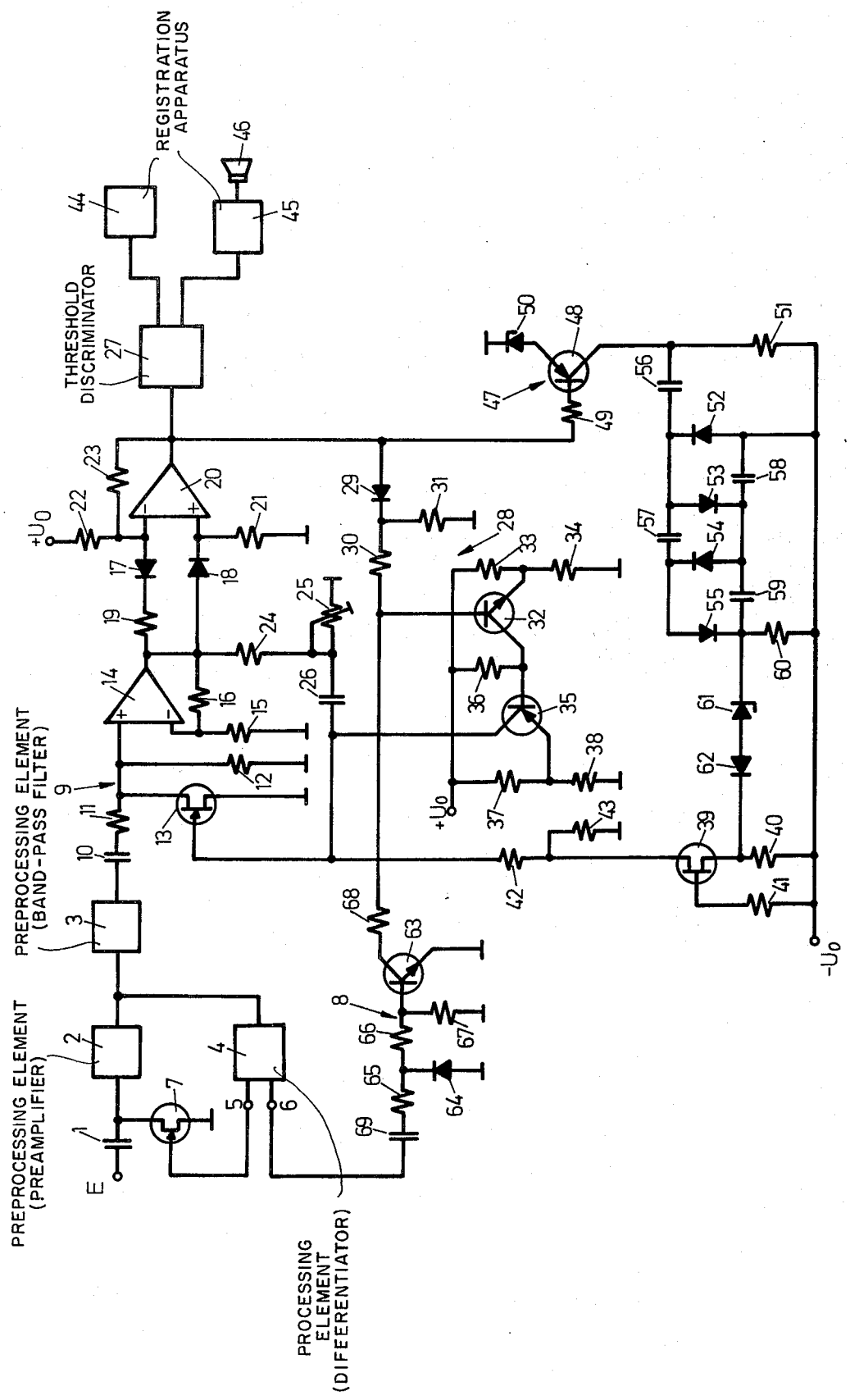

INSTALLATION FOR THE DETECTION AND PROCESSING OF ELECTRICAL SIGNALS

FIELD OF THE INVENTION

The present invention relates to an installation for the detection and, respectively, processing of electrical signals, in particular, physiological measuring signals, for example EKG, through the intermediary of a filter arrangement located in the measuring signal channel which is determinative of desired frequency components of the signals.

Electrical signals, particularly physiological measuring signals, frequently evince different frequency components at relatively extensively oscillating amplitudes. However, for the further utilization thereof frequently of interest are, however, signal components which have definite amplitudes and frequencies. One such instance is encountered, for example, in the EKG-measuring technology wherein, in the normal case there is to be extracted only the R-wave or curve which is of large amplitude and adsorbed with high frequency components, whereas other amplitude components whose amplitude, depending upon circumstances, may even be elevated to the range of the R-display or wave amplitude, but whose frequency components differ from the frequency components of the R-display or wave (for example T-, or P-wave), must be damped as extensively as possible.

DISCUSSION OF THE PRIOR ART

In order to filter out the interesting signal components, with concurrent damping of the signal components which are not of interest, there have heretofore been employed installations of the above-mentioned type with frequency filter arrangements, in which the frequency characteristic of the known filter arrangements is rigidly so adjusted, whereby the frequency components of interesting signal amplitudes fall within the transmission range whereas, in contrast therewith, frequency components signal amplitudes which are not of interest fall within the damping range of the filter. In installations for EKG-processing, the transmission range of currently used filter arrangements lies, for example, in a range above 8 Hz. Since the R-displays or curves of the EKG, in the normal case, indicate essentially frequencies above 8 Hz, the R-display or wave is, accordingly transmitted or passed through almost undamped. Other amplitude components such as, for example, the T- or P-waves, whose frequencies, in the normal case, lie below 8 Hz, are in contrast therewith damped to a minimum value.

The employment of filters which are defined in this manner affords a sufficient degree of measuring assurance, as long as the electrical signals conform to the normal form within predetermined ranges. Through the term "normal form" there is to be hereby understood that the interesting signal components of the electrical signals remain essentially constant in their amplitudes, as well as in their frequency content.

In actual practice it is, however, a fact that these above-mentioned requirements can never be accurately maintained. Particularly in the EKG-measuring technology it quite frequently occurs that the amplitudes of EKG signals are subjected to considerable oscillations. As long as the R-display or wave of that type of EKG further corresponds in its frequency to a normal R-display, then this R-display will also pass through the filter arrangement and will be evaluated as the R-display or wave. However, the danger is present that, in general, for extremely high-amplitude EKG signals additionally the T- or P-waves, notwithstanding damping by means of the filter arrangement, are still so high-amplituded so as to be confused with the R-displays or waves of the signals. In the reverse instance, physiological signals, in particular also EKG signals, may be, however, so extensively degenerated to thereby evidence only abnormally low amplitudes, and to additionally primarily lie with their frequency contents outside of the transmission range of the filter arrangement. In particular, in the EKG diagnostic, that type of continuous abnormally low amplitude component signifies the presence of medical danger which requires the initiation of extensive measures for therapeutic assistance. Particularly in such examining instances in which the physician or the specialized operating personnel does not directly observe the measuring process at the patient, but in which this measuring process is carried out automatically through the respective installation, then the occurrence of that type of instance of danger must also be necessarily automatically recognized by the installation and for example, indicated through actuation of a respective alarm. That type danger case which threatens the life of a patient, for example, always occurs at a flickering EKG. Since flickering waves in most instances evidence a very much lower amplitude (at most, for example, one-third of a normal R-display amplitude) and concurrently evidence a low-frequencied frequency content as usual QRS-complexes, these flicker waves could not be dependably diagnosed by means of the known installations of the above-mentioned type inherently as true flicker waves which require completely specialized therapeutic countermeasures (defilibration), since they were either initially completely suppressed by the filter arrangement which was primarily set to the R-displays or under circumstances at incomplete suppression, for example, due to considerable amplitude oscillations at concurrently applied relatively low basic damping of the filter arrangement, evaluated by being singled-out QRS-complexes having a more or less uneven rhythm.

SUMMARY OF THE INVENTION

Accordingly, it is an object of the present invention to provide an installation of the above-mentioned type which avoids the aforementioned disadvantages, meaning, that for amplitude oscillations which are too extremely high, as well as for amplitudes which are too abnormally low, at an eventually concurrent displacement of the frequency content of these amplitudes, there is facilitated the unambiguous and clear selection of the interesting signal amplitude components from those which are not of interest, and particularly also in the instance when the interesting signal component affords a distinction between the normal case and the case of medical danger.

The aforementioned object is inventively achieved in that the filter arrangement encompasses controllable means for the variation of the frequency range, as well as for the damping of the transmitted signal components; and which provides a control installation for effecting the control of the controllable means in dependence upon the signal amplitudes in the sense whereby the transmission frequencies of the filter arrangement at signals with the normal case, relatively high or in contrast therewith still higher signal amplitude components, at an increase of the transmission damping, may be displaced in the direction of frequencies which are essentially significant for these high signal amplitude components; and for signals with abnormally low signal amplitude components, at a reduction of the transmission damping, may be displaced in the direction of frequencies which are essentially significant for these low signal amplitude components.

The installation, in accordance with the invention, through the automatic damping compensation and concurrent frequency range regulation, in dependence upon the signal amplitudes, facilitates the selection of interesting signal amplitudes in the range of relatively higher as well as in the range of abnormally lower amplitude components. In particular, in EKG-processing thereby is thus provided, for example, the capability of clearly selecting these amplitudes, even at extensively oscillating R-display amplitudes, from other signal components which are not of interest, for example, P- or T-waves, and due to their relatively regular occurrences evaluate them as genuine R-displays or waves. Concurrently, there is also produced the ability that, in case of the presence of flicker waves (instance of danger), the amplitude of these waves may be extensively ascertained, and on the basis of the criterion of the high frequency of occurrence with concurrent occurrence discontinuity, to now be clearly and unambiguously diagnosed as flicker wave amplitudes.

BRIEF DESCRIPTION OF THE DRAWING

Further advantages and details of the invention may now be ascertained from the following description of an exemplary embodiment (for example, in connection with EKG-processing), taken in conjunction with the accompanying single FIGURE of the drawing which schematically illustrates a circuit diagram of the invention.

DETAILED DESCRIPTION

In the installation as shown in the FIGURE of the drawing, EKG signals are applied to an input E. From there they are separately transmitted through an input capacitance 1, as well as through a first preprocessing element 2 which, in the usual manner, includes a preamplifier, to respectively second and third preprocessing elements 3 and 4. The second preprocessing element 3 hereby incorporates the usual active band-pass filter with pulse frequencies of, for example, 4 Hz and 23 Hz. The band-pass filter is transmissive for QRS-complexes, as well as for P- and T-waves of the EKG, and also for flicker or scintillation waves. The third preprocessing element 4, in contrast therewith, for example, incorporates a differentiating element with a subsequent full-wave rectifier, amplitude discriminator, as well as a monostable flip-flop or stepping oscillator. If pacemaker impulses, for example, coincide with the EKG signals, then the preprocessing element 4 discriminates these due to their larger increase steepness at the subsequently awaited amplitude of the EKG signals (the R-displays) of comparable amplitude values so that an output signal is produced at the output 5 through the intermediary of the monostable flip-flop. This output signal serves as the drive-control impulse for a field-effect transistor 7, the latter of which is connected to the input of the preprocessing element 2, which is thereby controlled into a conductive condition for the short-circuiting and the consequent elimination of the pacemaker impulses from the EKG. Concurrently with the drive-control impulse for the transistor 7, at the output 6 of the element 4 there is also generated an impulse for actuation of a threshold-frequency oscillator 8, which is described in greater detail hereinbelow.

The frequency-trimmed EKG signals which are received at the output of the preprocessing element 3 are than transmitted to the non-inverting input of an operational amplifier 14 through a high-pass filter 9 which includes a series capacitance 10 as well as a subsequent voltage divider for the EKG signals consisting of an ohmic series resistance 11, as well as an ohmic shunt resistance 12 with a parallel positioned field-effect transistor 13. The inverting input of this amplifier 14 thereby is connected, on the one hand, across the resistance 15 with the ground and, on the other hand, through the resistance 16 with the amplifier output. The resistances, as well as the capacitance of the high-pass filter 9, are collectively so dimensioned that for the switched-in transistor 13, the lower limiting frequency of the filter, 9 at a maximum dividing ratio for the voltage divider (maximum transmission damping of the filter), evidences a maximum value of approximately 8 Hz, and for the blocked transistor 13 at a minimum dividing ratio, the voltage divider (minimum transmission damping of the filter), evidences a minimum value of approximately 4 Hz.

The signals which appear at the output of the operation amplifier 14 are transmitted, on the one side, to a full-wave rectifier which is constructed of diodes 17 and 18, a series resistance 19, as well as an amplifier 20 with the switching resistances 21, 22, 23; and, on the other side transmitted through a voltage divider 24, 25 to a condenser 26. The amplifier 20 of the full-wave rectifier, at positive EKG signals, operates as a non-inverting and, conversely, at negative signals, as an inverting amplifier. Accordingly, it causes across the resistances 22, 23 which are applied to the voltage $+ U_0$, a displacement of the zero line of the amplifier output signals in a negative direction for a constant amount. The amount of the zero displacement thereby is so selected, so that in the normal instance the R-displays of the EKG signals at the output of the full-wave rectifier at a conductive transistor 13 of the high-pass filter 9 still lies above the positive threshold (for example, + 1 volt) of a first threshold discriminator 27, as well as also lying for a blocked transistor 13 above a therewith comparably higher threshold (for example, + 4 volts) of a second threshold discriminator 28.

The first threshold discriminator 27 essentially consists of a monostable flip-flop, which generates an output signal upon the respective exceeding of its input threshold generates by the EKG signals. The second threshold discriminator 28 consists of a diode 29, a voltage divider 30, 31, as well as a base-emitter section of a transistor 32, inclusive of a voltage divider 33, 34 for the emitter bias voltage connected to this transistor on the emitter side thereof and lying at the voltage $+ U_0$ voltage. The transistor 32 additionally, together with a further transistor 35 having switching resistance 36, 37, 38, forms a control voltage amplifier. This control voltage amplifier, in conjunction with the previously described condenser 26, generates a control voltage (which is supplied with a portion of the output voltage of the amplifier 14 for improved signal linearization) at the field-effect transistor 13 of the high-pass filter 9, which controls the transistor 13 in dependence upon the signal amplitudes at the input of the threshold discriminator 28 towards higher or lower resistance values. The dependence of the control upon the input signal of the threshold discriminator 28, which corresponds to the output signal of the full-wave rectifiers 17 to 23, is hereby obtained as follows:

When the EKG signal of the full-wave rectifiers 17 to 23 lies below the threshold of the threshold discriminator 28, then the condenser 26 is charged to a negative voltage value through a charging installation-$U_0$, 39, as well as 40 through 43 (wherein the element 39 represents a control field-effect transistor for the operative point control of the field-effect transistor 13 in the high-pass filter 9, and the elements 41 through 43 represent ohmic resistances), which as bias voltage-blocking value maintains the field-effect transistor 13 at a high resistance value. This resistance value is so selected through the bias voltage-blocking value, that flicker waves which pass through the high-pass filter 9 indicate an amplitude at the output of full-wave rectifiers 17 to 23 at an amplitude which, in all instances, still lies above the threshold of the threshold discriminator 27. When, in contrast therewith, the output signal of the full-wave rectifier 17 to 23 exceeds the threshold of the threshold discriminator 28 (this case is encountered at least during the occurrence of an R-display in the EKG), then the voltage of the voltage divider 33, 34 will inclusively exceed the switching voltages of the transistor 32, as well as that of diode 29. The transistor 32 becomes conductive and correspondingly controls the transistor 35 of the control voltage amplifier into a conductive condition. The condenser 26 thereby is rapidly discharged to a positive value across the collector-emitter section of the transistor 35 so that the field-effect transistor 13 in the high-pass filter 9 is equally rapidly regulated to lower resistance values. Through the herewith following increase in the transmission damping of the high-pass filter 9, the EKG signals at the output of the full-wave rectifiers are now extremely rapidly damped to such an extent, until the R-display or wave runs closely below the threshold value of the threshold discriminator 28. Concurrent with the increased damping, there follows an increase in the lower limit frequency of the high-pass filter 9 from approximately 4 Hz to approximately 8 Hz.

The control voltage amplifier 32, 35 through 38 thereby, in operative connection with the threshold discriminator 28, as well as the condenser 26 and through the field-effect transistor 13 in the high-pass filter 9, controls the frequency width and the transmission damping of the filter 9 so that, for a normal EKG (also at extensively oscillating amplitudes), the total EKG is damped such a value, whereby the R-displays or waves are levelled essentially to values closely below the threshold of the threshold discriminator 28. Through the concurrent displacement of the lower limit frequency of the high-pass filter 9 in the direction of the frequency value which is significant for the R-display, there is additionally increased the amplitude distance between the R-display and the P- and, respectively, T-wave. At the threshold discriminator 27 there appear accordingly essentially only clear selected R-display amplitudes which, due to the regular exceeding of the threshold of the threshold discriminator 27, may be registered as genuine R-displays at an indicator or, respectively, registration apparatus 44. If in contrast therewith, flicker waves appear at the output of the full-wave rectifiers 17 to 27, then in the normal case, the amplitude thereof remains continually below the threshold of the threshold discriminator 28 (the amplitudes of flicker waves on an average are one-third of the R-display amplitude in the normal EKG). The condenser 26 is maintained at the bias voltage value of the field-effect transistor 13 (closing voltage value) due to the blocked transistor 35.

The high resistance value of the field effect transistor 13 causes that, on the one hand, the transmission damping value of the high-pass filter 9 is reduced to its minimum value and, concurrently, the lower limit frequency of the frequency values which are significant to the flicker waves is opened (reduction of the lower frequency to about 4 Hz). The flicker waves may thereby pass practically undamped through the high-pass filter 9. Correspondingly, the undamped amplitudes of the flicker waves at the output of the full-wave rectifiers 17 to 23 thereby still also lie above the threshold of the threshold discriminator 27. Since the flicker waves now relatively frequently exceed the threshold of the threshold discriminator 27, with the occurrence of the waves in opposition to the normal QRS complexes in EKG is, however, primarily discontinuous, due to occurrence frequency criterium at a concurrent occurrence discontinuity, the presence of the flicker waves may now be clearly recognized, for example, through the registration apparatus 45 and, in conformance therewith, an acoustic or any kind of alarm (for example, a loudspeaker 46) may be activated.

In addition to the two threshold discriminators 27 and 28, there is also connected to the output of the full-wave rectifiers 17 to 23, a third threshold discriminator 47 which includes the transistor 48, the base resistance 49, and the emitter-zener diode 50. This threshold discriminator 47, in contrast with the thresholds of the discriminators 27 and 28, evidences a very much lower signal threshold lying in the negative range (for example, at $-3$ volts). The threshold discriminator 47, on the output side thereof, is connected across a resistance 51 to a voltage multiplier (diode pump) having diodes 52 through 55, capacitances 56 through 59, as well as a load resistance 60. The output of this voltage multiplier, in turn, is coupled across a zener diode 61, as well as semi-conductor diode 62 directly to the source of the previously mentioned field-effect transistor 39 which serves as the operative point control transistor for the field-effect transistor 13 of the high-pass filter 9.

The threshold discriminator 47, together with the voltage multiplier 52 through 60, serves as a control voltage amplifier for the blacking-out of higher-frequency static which is continually superimposed on the EKG signals (for example, power supply hum). The blacking-out of the static functions herein as follows:

When that kind of static occurs in the EKG signal at the output of the full-wave rectifiers 17 to 23 (for example, power supply hum), then the amplitude of this static unequally frequently exceeds the threshold of the threshold discriminator 47 such as, for example, the R-display of the normal EKG. Detrimentally, within a short period, the transistor 48 is thus reversely controlled a number of times from a conductive into a blocked condition. At each new switching sequence of the transistor 48, a voltage increase occurs at the resistance 51 which effects the voltage multiplier in the sense in that, after a few switching pulses, there is formed a relatively high voltage at the load resistance 60 of the voltage multiplier. As soon as this voltage exceeds the zener voltage of the zener diode 61, as well as the switching voltage of diode 62, it exerts an effect on the field-effect transistor 13 across the control transistor 39 in a sense whereby this transistor 13 is so far regulated towards a positive bias voltage value and thereby to lower resistance values, until the amplitude of the static is regulated below the threshold of the threshold discriminator 47. By means of the threshold discriminator 47 with the subsequent voltage multiplier 52 through 60, as well as the operative point adjusting transistor 39 for the field-effect transistor 13 in the high-pass filter, the entire EKG signal is maintained so small from the beginning (initial damping), that a higher-frequency static of the previously mentioned type (for example, power supply hum) from the threshold discriminator 27 is not evalued as a phenomenon when it continuously occurs.

The already previously mentioned threshold-frequency oscillator 8 consists of a transistor 63, a diode 64, the resistances 65 through 68, as well as an input capacitance 69. If there appears a (negative) voltage impulse in the EKG signal at the output 6 of the element 4 due to the pacemaker impulses recognized in the preprocessing element 4, then the condenser 69 of the threshold-frequency oscillator is charged over to a negative value through the diode 64. After this impulse, the condenser 69 discharges across the base-emitter section of the transistor 63. The transistor 63 is hereby controlled for a predetermined time, preferably for 250 milliseconds, into a conductive condition. This has the effect that, for the same time period, meaning also for 250 milliseconds, the actuating threshold of the threshold discriminator 28, by means of resistances 68 and 30 which now operate as voltage dividers, is displaced towards higher values, preferably to double the normal value (from +4 volts to approximately +8 volts). This short-term threshold increase at each time after the occurrence of a pacemaker impulse has the advantage that immediately after, the heart action voltages occurring subsequent to pacemaker impulses with an amplitude which is inherently larger than the amplitude at self-excitation, are extensively damped within a short time. The danger that self-exciting heart action, which follows a heart action effected by pacemaker impulses, may be lost due to the long-durational strong damping at a low threshold of the threshold discriminator 28 (at +4 volts), is thus no longer present.

While there has been shown what is considered to be the preferred embodiment of the invention, it will be obvious that modifications may be made which come within the scope of the disclosure of the specification.

What is claimed is

1. In an installation for the detection and processing of electrical signals, in particular physiological measuring signals such as EKG, including a filter arrangement located in the measuring signal channel which is determinative of the desired frequency components of the signals; and a threshold discriminator for the filter output signals, the improvement comprising: said filter arrangement including a voltage divider having a voltage-controlled variable resistance, said voltage divider forming control means for varying the frequency range and the filter damping of passed-through signal components; a control voltage generator, said control voltage generator generating a control signal at signal amplitudes above the threshold of said threshold discriminator for displacing the variable resistance in the voltage divider of said filter arrangement so that the signal components previously lying above the threshold of said threshold discriminator are damped below the threshold by said voltage divider while the frequency range of said filter arrangement is concurrently displaced to higher frequencies, and at signal amplitudes lying continually below the threshold of said threshold discriminator the control signal of said control voltage generator disappears whereby, with the disappearance of said control signal, said filter arrangement is controlled to lower degrees of transmission damping through the variable resistance of said voltage divider for raising the lower signal components in a direction towards the threshold of said threshold discriminator while concurrently displacing the frequency range of said filter arrangement towards lower frequencies.

2. Installation as claimed in claim 1, said filter arrangement and said controllable voltage divider being constructed for narrowing the transmission frequencies of said filter arrangement at high signal ampliitude components above the threshold of said threshold discriminator to frequencies essentially significant to said high signal amplitude components, and for widening said transmission frequencies at low signal amplitude components below the threshold of said threshold discriminator to frequencies essentially significant to said low signal amplitude components.

3. Installation as claimed in claim 1, said filter arrangement and said controllable voltage divider being constructed to effect controls for raising the transmission damping of said filter arrangement to a maximum value at said high signal amplitude components above the threshold of said threshold discriminator, and for reducing the transmission damping to a minimum value at said low signal amplitude components below the threshold of said threshold discriminator.

4. Installation as claimed in claim 3, said controllable voltage divider correlating the maximum value and minimum value of the transmission damping with each other so that the amplitude value of said high signal component damped with the maximum value corresponds to the amplitude value of the said signal component damped with the minimum value.

5. Installation as claimed in claim 1, said filter arrangement having a minimum value for the transmission damping selected so that the low signal components after transmission through said filter arrangements have the amplitude thereof located essentially closely below the threshold of said threshold discriminator.

6. Installation as claimed in claim 1, said voltage-controlled variable resistance being built into said voltage divider so that a reduction in the resistance value of the latter effects an increase in the dividing ratio of the voltage divider with a concurrent increase in the lower limit frequency of a high-pass filter in said filter arrangement, and an increase in the resistance value effects a reduction in the dividing ratio of the voltage divider with a concurrent reduction in the lower limit frequency of said high-pass filter.

7. Installation as claimed in claim 6, said high-pass filter comprising a capacitive series element having ohmic series and shunt resistances connected thereto for forming said voltage divider, and said voltage-controlled variable resistance being a field-effect transistor connected in parallel to said shunt resistance.

8. Installation as claimed in claim 7, said field-effect transistor having a control electrode; a condensor being connected to said electrode so as to form control means for controlling said transistor, said condensor having a discharge arrangement, said condensor being charged to a bias voltage value for maintaining said transistor at a high resistance value, such as a transistor blocking-voltage at signals below the threshold of said threshold discriminator, and being discharged at signals above the threshold by said discharge arrangement at increasing control voltage values of said transistor.

9. Installation as claimed in claim 8, said discharge arrangement comprising a control voltage amplifier having at least one charging transistor, said transistor being controlled into a conductive condition upon the electrical signal exceeding the threshold of said threshold discriminator and the condensor discharges through its collector-emitter section to an extent until the signal again drops below the threshold.

10. Installation as claimed in claim 9, said condensor being discharged at considerably lower time constants than the charging thereof.

11. Installation as claimed in claim 9, said control voltage amplifier comprising an input transistor forming said threshold discriminator in conjunction with an emitter-sided voltage divider for the emitter bias voltage and a base-sided voltage divider having a blocking diode for the electrical signal, and including a switching transistor for switching in of the charging transistor for the condensor upon exceeding a signal threshold value.

12. Installation as claimed in claim 8, comprising an operative point control transistor including a field-effect transistor, said condensor and field-effect transistor in said high-pass filter being actuated by a bias voltage generator for variation of the condensor-bias voltage values for the high transistor resistance.

13. Installation as claimed in claim 12, comprising frequency voltage converter receiving said electrical signal being connected to said operative point control transistor and adapted to detect the incidence frequency of significant amplitude values in the electrical signal and to generate an output voltage in correspondence with said incidence frequency, said control transistor controlling the field-effect transistor in said high-pass filter in dependence upon this output voltage for so long in the direction of lower resistance values until the incidence frequency of the significant amplitude values at the frequency voltage converter drops below a predetermined minimum value.

14. Installation as claimed in claim 13, comprising a second threshold discriminator for detecting the occurrence of the significant signal values at said frequency voltage converter, said threshold discriminator having the threshold thereof adjusted to said significant signal values.

15. Installation as claimed in claim 14, said threshold of said second threshold discriminator being adjusted to a significant value which lies in the range of the expected highest amplitude of continually occurring static voltage, such as power supply hum, which is superimposed on the inherent electrical signal.

16. Installation as claimed in claim 14, said second threshold discriminator comprising a transistor forming a threshold switch, said transistor adapted to be controlled into a conductive condition upon the transistor input voltage exceeding the switching voltage of said transistor inclusive the zener voltage of a zener diode located in the emitter circuit of said transistor.

17. Installation as claimed in claim 16, comprising a voltage multiplier including series capacitances and parallel diodes, said transistor being connected to said voltage multiplier across a collector resistance, said voltage multiplier forming said frequency voltage converter; and an output resistance having a voltage generated therein by said voltage multiplier increasing with the switching pulse of said second threshold discriminator.

18. Installation as claimed in claim 17, comprising diode switching means including a zener diode with a reverse-poled normal semiconductor diode, said output voltage of said voltage multiplier being connected to the source of said control transistor through said diode switching means, said control transistor controlling the field effect transistor of said high-pass filter to higher resistance values for a period until the output signal of the voltage multiplier exceeds the switching voltage of said diode switching means.

19. Installation as claimed in claim 1, comprising a measuring element connected into the measuring signal channel preceding the high-pass filter for detecting the presence of signal components having considerably increased amplitudes in contrast with normal amplitudes; and a threshold regulator for raising the threshold of the threshold discriminator associated with the control installation for the control of the field-effect transistor in said high-pass filter for a predetermined time interval to a value higher in comparison with a normal value.

20. Installation as claimed in claim 19, comprising a discriminating and blacking-out arrangement for the detection of and blacking-out of pacemaker impulses superimposed on EKG signals, said discriminating and blacking-out arrangement generating an output signal for said threshold regulator upon each occurrence of a pacemaker signal so as to raise the threshold of said threshold discriminator to twice the normal value for a period of 250 milliseconds.

21. Installation as claimed in claim 20, said threshold regulator comprising a transistor having a charging condensor, said charging condensor being charged through a seminconductor diode to a predetermined value by the output signal of said pacemaker impulse detecting and blacking-out arrangement and being controlled into a conductive condition upon the subsequent discharge of said transistor; and a voltage divider being actuated in response thereto for raising the threshold of said threshold discriminator.

\* \* \* \* \*